(12) United States Patent
Crosby et al.

(10) Patent No.: US 9,578,874 B2
(45) Date of Patent: Feb. 28, 2017

(54) METHODS AND COMPOSITIONS FOR REDUCING OR INHIBITING SPRAY DRIFT AND DRIFTABLE FINES

(71) Applicant: Adjuvants Unlimited, LLC, Memphis, TN (US)

(72) Inventors: Kevin E. Crosby, Germantown, TN (US); Richard W. Fraley, Hernando, MS (US); Gregory M. McManic, Germantown, TN (US); Mickey R. Brigance, Germantown, TN (US); Jennifer Bear, Cordova, TN (US)

(73) Assignee: ADJUVANTS UNLIMITED, LLC, Memphis, TN (US)

( * ) Notice: Subject to any disclaimer, the term of this patent is extended or adjusted under 35 U.S.C. 154(b) by 0 days.

(21) Appl. No.: 13/940,898

(22) Filed: Jul. 12, 2013

(65) Prior Publication Data
US 2014/0018240 A1 Jan. 16, 2014

Related U.S. Application Data

(60) Provisional application No. 61/670,703, filed on Jul. 12, 2012.

(51) Int. Cl.
*A01N 25/04* (2006.01)
*A01N 25/10* (2006.01)
*A01N 25/02* (2006.01)
*A01N 57/20* (2006.01)

(52) U.S. Cl.
CPC ............ *A01N 25/10* (2013.01); *A01N 25/02* (2013.01); *A01N 25/04* (2013.01); *A01N 57/20* (2013.01)

(58) Field of Classification Search
CPC ......... A01N 25/10; A01N 25/04; A01N 25/24
See application file for complete search history.

(56) References Cited

U.S. PATENT DOCUMENTS 3,175,898 A * 3/1965 Seymour et al. ............. 504/145
3,592,910 A * 7/1971 Clark et al. ................... 514/481

OTHER PUBLICATIONS

Product data sheet for PICCOLYTE A25 [online], (Jul. 2011), retrieved from the internet from URL <http://www.pinovasolutions.com/products/piccolyte-a25>.*
"POLYOX Water-Soluble Resins: Unique Resins for Binding, Lubricity, Adhesion and Emollient Performance", by The Dow Chemical Company, published Mar. 2002.

* cited by examiner

*Primary Examiner* — Abigail Fisher
*Assistant Examiner* — Daniel Branson
(74) *Attorney, Agent, or Firm* — Smith, Gambrell & Russell, LLP

(57) ABSTRACT

Disclosed herein are methods and compositions for reducing or inhibiting spray drift and driftable fines.

15 Claims, No Drawings

METHODS AND COMPOSITIONS FOR REDUCING OR INHIBITING SPRAY DRIFT AND DRIFTABLE FINES

CROSS-REFERENCE TO RELATED APPLICATIONS

This application claims the benefit of U.S. Provisional Application No. 61/670,703, filed 12 Jul. 2012, which is herein incorporated by reference in its entirety.

BACKGROUND OF THE INVENTION

1. Field of the Invention

The present invention relates to agricultural compositions and tank mix adjuvants, which exhibit reduce amounts of fine particles when sprayed through spray nozzles used in agriculture to disseminate agrochemicals.

2. Description of the Related Art

In the agricultural arts, various agrochemicals are applied to growing areas by spraying. The growing areas may be crop areas in the field, which can be very large, or smaller growing areas such as those in greenhouses. The agrochemicals applied as sprays include fertilizers, herbicides, fungicides, insecticides, pesticides, miticides, micronutrients, and the like. These materials can be applied to the target surfaces including the plants, seeds, crops, and/or the soil. The agrochemicals must be applied via a carrier and reach the target surfaces to exert their desired biological effects. As the term is used herein, "pesticide" includes herbicides, insecticides, fungicides, miticides, and plant growth regulators. Fertilizers include macronutrients (containing Nitrogen, Phosphorus, Potassium, Sulfur, Calcium, Magnesium), and micronutrients.

Certain pesticides (particularly those containing 2,4 D, dicamba and glyphosate salts, esters, and acids) are known to cause adverse effects if these pesticides inadvertently come in contact with non-target plants. When agricultural chemicals are sprayed, a distribution of spray particle sizes is formed and this distribution depends on the nature of the spray mix, type of nozzle used, spray system pressure and other variable factors such ground speed of the applying system, natural wind speed, temperature, and humidity. One possible side effect of the spraying process is an undesirable effect commonly called spray or pesticide drift. Controlling spray drift of these pesticides is especially important as genetically modified crop plants resistant to these pesticides are commercialized.

The importance of drift control is well recognized by the agricultural industry as a number of technologies have been developed based on the following technologies: 1) polyacrylamide polymers, 2) invert emulsion technology, 3) Guar gums, and 4) Lecithin. Each of these technologies is used in practice, but each technology has limitations on their use. Furthermore, the importance of drift control is such that regulatory agencies such as the United States Environmental Protection Agency have promulgated rules to minimize such drift. As a consequence, pesticide products often have labels detailing use restrictions so as to reduce drift potential of a pesticide spray.

Therefore, a need exists for methods and compositions for controlling spray drift of pesticides and other compositions to adjacent crops.

SUMMARY OF THE INVENTION

In some embodiments, the present invention is a composition which has a reduced amount of driftable fines or is capable of reducing the amount of driftable fines of an agrochemical when mixed therein (e.g., as a tank mix adjuvant) as compared to a control. In some embodiments, where the composition is ready to use, i.e., is not to be mixed with other compositions before spraying, the composition comprises at least 0.01% by weight, preferably about 0.01%-2.0% by weight, and more preferably about 0.02%-0.12% by weight, of a resin. In some embodiments, the resin is a phenolic resin, a rosin ester, or a polyterpene. In some embodiments where the composition of the present invention is a concentrate that is to be used as an additive, e.g., a tank mix adjuvant, that is added to an agrochemical before the agrochemical is sprayed, the concentrate comprises a concentrated amount of the resin which results in at least 0.01% by weight, preferably about 0.01%-2.0% by weight, and more preferably about 0.02%-0.12% by weight, of the resin in the final mixture comprising the agrochemical that is sprayed. In some embodiments, the concentrate comprises at least 1% by weight, preferably about 5%-50% by weight, more preferably about 15%-25% by weight, and most preferably about 20% by weight, of a resin. According to the present invention, the compositions and final mixtures to be sprayed have an enhanced ability to stick to plant surfaces and are compatible for use with agrochemicals, e.g., the compositions and final mixtures to be sprayed do not have a detrimental effect on the activity and/or function of agrochemicals. The concentrates of the present invention may be incorporated into pesticide formulations ("in can") or added to spray tank mixtures ("tank mix additives"). In some embodiments, the concentrates of the present invention are adjuvants that can be mixed with an agrochemical, e.g., one, two, or three or more pesticides, into the spray mixture without causing mixing issues such as flocking, thickening of the spray mixture, and pesticide actives precipitation. The concentrates according to the present invention may be homogenous compositions.

In some embodiments, the present invention provides methods of reducing, inhibiting, or preventing driftable fines (mean particle size <150 microns) from forming when spraying an agrochemical using conventional spraying techniques and spraying apparatuses used in the agrochemical arts. In these embodiments, the methods comprise adding at least one resin, e.g., a phenolic resin, a rosin ester, or a polyterpene, to the agrochemical before spraying. In some embodiments, the amount of the resin added to the agrochemical is one that results in at least 0.01% by weight, preferably about 0.01%-2.0% by weight, and more preferably about 0.02%-0.12% by weight, of the resin in the total composition to be sprayed. In some embodiments, the methods of the present invention results in an improved deposition of an agrochemical onto plant foliage or soil by increasing the percent of total spray droplets of the agrochemical that is deposited on the target substrate and do not drift.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DETAILED DESCRIPTION OF THE INVENTION

The present invention is directed to compositions, concentrates, and methods for controlling spray drift. Compositions according to the present invention that are ready to be sprayed "as is" comprise at least 0.01% by weight, preferably about 0.01%-2.0% by weight, and more preferably about 0.02%-0.12% by weight, of at least one resin, and at least one agrochemical and/or at least one adjuvant. The compositions of the present invention have a reduced amount of driftable fines when sprayed as compared to a control, i.e., composition that does not contain the resin. As used herein, "driftable fines" are droplets of the spray that are less than 150 microns in diameter. The amount of driftable fines is a parameter that influences pesticide drift. The larger the amount of driftable fines, the greater the amount of pesticide drift.

In some embodiments, the concentrates of the present invention reduce, inhibit, and/or prevent the spray drift of a second composition when added thereto as compared to the spray drift of the second composition without having the concentrate mixed therein. In some embodiments, concentrates according to the present invention comprise a concentrated amount of at least one resin which results in at least 0.01% by weight, preferably about 0.01%-2.0% by weight, and more preferably about 0.02%-0.12% by weight, of the at least one resin when mixed with the second composition. In some embodiments, the concentrate comprises at least 1% by weight, preferably about 5%-50% by weight, more preferably about 15%-25% by weight, and most preferably about 20% by weight, of a resin. In some embodiments, the concentrates may comprise at least one agrochemical and/or at least one adjuvant. In some embodiments, the concentrates of the present invention reduce, inhibit, and/or prevent the amount of driftable fines of a second composition when added thereto and sprayed as compared to the amount of driftable fines of the second composition when sprayed without having the concentrate mixed therein. In some embodiments, the concentrates of the present invention may be readily mixed with agrochemicals such as fertilizers, pesticides, adjuvants (which may be concentrated), and/or water and then applied to a target area using a spraying apparatus, e.g., a spray nozzle.

As used herein, an "agrochemical" refers to pesticides (insecticides, herbicides, miticides, fungicides), plant growth regulators, fertilizers, and micronutrients, and the like. As used herein, an "adjuvant" refers to a material added to a tank mix to aid or modify the action of an agrichemical, or the physical properties of the mixture (see ASTM Standard E1519-10, 2010, "Standard Terminology Relating to Agricultural Tank Mix Adjuvants", ASTM International, West Conshohocken, Pa., 2010, which is herein incorporated by reference). Adjuvants may be in the form of a liquid, a dry powder, or a granule. Adjuvants are available to both the agricultural and nonagricultural markets. Adjuvant types include crop oil concentrates, nonionic surfactant blends, drift control agents, compatibility agents, water conditioning agents, and the like.

Resins suitable for use according to the present invention include those that are known in the art and are sold, for example, by Akzo Nobel Inc. as WITBREAK RESINS, Arizona Chemical as SYLVARES and SYLVATAC resins, Pinova Corp as PICOLYTE resins, and Eastman Chemical. Particularly preferred resins according to the present invention include phenolic resins, rosin esters, and polyterpenes. Phenolic resins include those that are reaction products of formaldehyde and phenols. An example of a phenolic resin is WITBREAK DRC 167, which is a polymer of formaldehyde, polymer with methyloxirane and 4-nonyphenol. Rosin esters include those that are the reaction products of rosin and an alcohol. Polyterpenes are polymers of isoprene or polyisoprene.

The compositions and concentrates of the present invention may be in the form of an aqueous solution (AS), an essentially non aqueous solution containing less that 10% water (NAS), a concentrated emulsion (CE), a suspo-emulsion (SE), a dispersion, a reverse phase emulsion (RPE), an emulsifiable concentrate (EC), a micro-emulsifiable concentrate (MEC), and the like.

The compositions and concentrates of the present invention may contain nonionic surfactants, anionic surfactants, cationic surfactants, organosilicones, quaternary compounds, dispersants, and/or other surface-active agents. The compositions and concentrates of the present invention may contain plant nutrients such as nitrogen compounds, phosphorous compounds, potassium compounds, and minor elemental compounds of zinc, iron, manganese, magnesium, boron, and the like. The compositions and concentrates of the present invention may contain other functional agents including defoamers, petroleum distillates, vegetable derived oils, fatty alcohols, polyhydric alcohols, glycol ethers, humectants, polymers, and the like. The concentrates according to the present invention may be diluted, with water for example, before for spraying and/or mixing with an agrochemical.

In some embodiments, the compositions and concentrates of the present invention do not interfere with and/or reduce the activity of agrochemicals, e.g. pesticides, when mixed therewith. Thus, the present invention provides drift control agents and compositions that are compatible with different types of agrochemical formulations (e.g., aqueous and oil based formulations).

In some embodiments, the present invention is directed to methods of reducing, inhibiting, or preventing the amount of spray drift and/or driftable fines of an agrochemical when sprayed which comprises adding an amount of at least one resin to result in at least 0.01% by weight, preferably about 0.01%-2.0% by weight, and more preferably about 0.02%-0.12% by weight, of the at least one resin in the final mixture to be sprayed.

In some embodiments, the present invention results in at least about a 0.5% reduction, preferably at least about a 1% reduction, more preferably at least about a 3-5% reduction in the amount of particles that are less than 150 microns in diameter. In some embodiments, the present invention results in about a 1-10% reduction in the amount of particles that are less than 150 microns in diameter.

Formulation (Concentrate) Examples

TABLE 1

| | Formulation Number | | | | | | | | |
|---|---|---|---|---|---|---|---|---|---|
| Ingredient | 1 | 2 | 3 | 4 | 5 | 6 | 7 | 8 | 9 |
| Ethoxylated triglyceride Agnique SBO 10, BASF, Florham Park, NJ | 20 | 20 | 20 | — | 20 | 20 | — | 25 | 25 |
| Fatty acid blend XTOL 0621, Georgia Pacific, Decatur, GA | 10 | 10 | 10 | 10 | 10 | 10 | 6 | | — |
| Petroleum resin 1* Witbreak DRC 167, Akzo Nobel, Chicago, IL | 16 | — | — | | — | — | — | — | — |

TABLE 1-continued

| Ingredient | 1 | 2 | 3 | 4 | 5 | 6 | 7 | 8 | 9 |
|---|---|---|---|---|---|---|---|---|---|
| Petroleum resin 2* Witbreak DRC 164, Akzo Nobel, Chicago IL | — | 16 | 16 | — | — | — | 39 | 15 | 15 |
| Paraffinic oil Calpar 70, Calumet Specialties, Indianapolis, IN | 15 | 15 | 15 | 15 | 15 | — | 13 | — | — |
| Ethoxylated sorbitan monooleate Agnique SMO-20-u, BASF, Florham Park, NJ | 35 | 35 | 15 | 35 | 35 | 35 | — | — | — |
| Polyterpene, Sylvares TR A25, Arizona Chemical, Jacksonville, FL | — | — | — | — | — | 20 | — | — | — |
| Rosin ester, Sylvatac RE25, Arizona Chemical, Jacksonville, FL | — | — | — | — | 20 | — | — | — | — |
| Nonylphenol ethoxylate POE 9, Tergitol NP-9, Dow Chemical, Midland, MI | — | — | — | — | — | — | 22 | 25 | — |
| Nonylphenol ethoxylate POE 6 Tergitol NP-6, Dow Chemical, Midland, MI | — | — | — | — | — | — | 20 | — | — |
| 2-ethylhexanol ethoxylate POE 6, Ecosurf EH-6, Dow Chemical, Midland, MI | — | — | 20 | — | — | — | — | — | 25 |
| C12-C18 methyl ester ethoxylate POE 5, Agnique ME1218-5, BASF, Florham Park, NJ | — | — | — | 20 | — | — | — | — | — |
| Diethylene glycol, Diethylene glycol, Dow Chemical, Midland, MI | — | — | — | — | — | — | — | 25 | 25 |
| Solvent naptha heavy aromatic, Aromatic 150 ExxonMobil Houston, TX | 4 | — | — | 4 | — | — | 4 | — | — |
| Water | — | — | — | — | — | — | — | 10 | 10 |

*Chemical name: formaldehyde, polymer with 2-methyloxirane and 4-nonylphenol

In the table above the amounts are percent by weight of the numbered formulations (concentrates).

The formulations of Table 1 were added to a solution of water and pesticide in the concentration noted. In the Examples, the amount of the given formulation added is provided as the percent volume of the total volume of the composition to be sprayed, e.g., in Example 1, the amount of Formulation 2 is 0.25% volume of the total volume of the composition (Water+Formulation 2).

It should be noted that one of ordinary skill in the art can readily calculate the amount of resin required in a concentrate in order to provide, when diluted to a given dilution, the desired amount of the resin in the composition to be sprayed. For example, where 1 quart of a concentrate having 16% by weight of resin is to be added to 100 gallons of water, in order to obtain about 0.04% by weight of the resin in the composition to be sprayed, one can calculate as follows: 1 gallon of water=8.34 lbs, 100 gallons=834 lbs, 1 qt formulated product=2.085 lbs, but only 16% resin=0.3336 lbs resin, 0.3336/834=0.0004×100=0.04% actual resin.

The water used in all tests contained a total of 342 ppm of total water hardness. When sprayed, the drift control standard used was a commercial formulation of polyacrylamide (PAM) which was Magnafloc 351 from BASF Corporation, Florham Park, N.J. The following data shows the effect on particle size distribution as determined by a Malvern Spraytec or a Helos Sympatec laser diffractometer particle size analyzer. All studies were done with either an XR8002 or XR11002 flat fan nozzle at 40 psi spray pressure. All additives are added at a volume:volume ratio (noted in each data table) in a total spray volume of 10 gallons per acre. Pesticide amounts are noted in each table.

Example 1

| Sample | % droplets <150 microns |
|---|---|
| Water only | 50.8 |
| Water + Formulation 2 (0.25% v:v) | 34.2 |
| Water + standard PAM | 37.7 |

These results show that both the standard polyacrylamide and Formulation 2 can reduce % fine particles when water alone is sprayed. However, Formulation 2 results in a 3.5% decrease in driftable fines over PAM.

Example 2

| Sample | % droplets <150 microns |
|---|---|
| Water | 46.7 |
| Water + glyphosate (K salt, 1.7%) | 40.8 |
| Water + glyphosate (K salt, 1.7%) + Formulation 1 (1% v:v) | 31.1 |

These results show that Formulation 1 reduces the amount of driftable fines of a spray mixture by about 9.7%.

Example 3

| Sample | % droplets <150 microns |
|---|---|
| Water | 47.4 |
| Water + imidicloprid SC | 44.0 |
| Water + imidicloprid SC + Formulation 2 (1% v:v) | 34.0 |

These results show that Formulation 2 reduces the amount of driftable fines by about 10%. Also, Formulation 2 reduces fine particles of a spray of a suspension concentrate as compared to Example 3 which uses a water soluble formulation of glyphosate.

Example 4

| Sample | % droplets <150 microns |
|---|---|
| Water | 41.5 |
| Water + glyphosate (K salt, 1.7%) + dicamba (dimethylamine salt, 1.25%) | 39.6 |
| Water + glyphosate (K salt, 1.7%) + dicamba (dimethylamine salt, 1.25%) + Formulation 5 (0.5% v:v) | 30.0 |
| Water + glyphosate (K salt, 1.7%) + dicamba (dimethylamine salt, 1.25%) + Formulation 2 (0.5% v;v) | 32.0 |

These results show that Formulations 2 and 5 reduce the amount of driftable fines by about 7.6% to about 9.6%.

Therefore, the compositions and concentrates of the present invention may be used with agrochemicals in order to reduce or inhibit the amount of driftable fines and/or spray drift.

Because of the reduced amount of driftable fines and spray drift, more droplets will be deposited on the surfaces of an agricultural target (e.g., soil, water, plant foliage, insects, mites, fungal spores, fungal biomass, etc.). Therefore, the compositions, concentrates, and methods of the present invention also provides increased deposition of one or more agrochemicals and/or adjuvants on surfaces of agricultural targets.

The compositions that are ready to spray according to the present invention comprise at least about 0.01% by weight, preferably about 0.01%-2.0% by weight, and more preferably about 0.02%-0.12% by weight, of at least one resin, and concentrates according to the present invention comprise a concentrated amount of at least one resin which results in at least about 0.01% by weight, preferably about 0.01%-2.0% by weight, and more preferably about 0.02%-0.12% by weight, of the at least one resin when mixed with the second composition. For example, in some embodiments, a concentrate according to the present invention comprises a concentrated amount of at least one resin and a concentrated amount of at least one agrochemical or adjuvant, wherein the concentrated amount of the at least one resin is an amount that results in at least 0.01% by weight, preferably about 0.01%-2.0% by weight, and more preferably about 0.02%-0.12% by weight of the resin in the composition to be sprayed when the concentrate is diluted to give a concentration of the at least one agrochemical or adjuvant suitable for spraying on an agricultural target. In some embodiments, concentrates according to the present invention comprise at least about 1% by weight, preferably about 5%-50% by weight, more preferably about 15%-25% by weight, and most preferably about 20% by weight, of the at least one resin.

The compositions and concentrates according to the present invention may comprise one or more additional ingredients, such as those commonly used in agricultural compositions and formulations, including emulsifiers, surfactants, dispersants, adjuvants, humectants, preservatives, polymers, solvents, and the like. The compositions and concentrates of the present invention may have any suitable pH (one that is suitable for the intended result and compatible with the agrochemical being applied). In some embodiments, the pH is from 2 to 12.

The compositions and concentrates of the present invention may further comprise an oil component, and/or surfactants (nonionic, anionic surfactants, cationic surfactants) and/or a fertilizer. The fertilizer can be present in an amount of 0.0001 to 99% by weight of the final spray mixture. Suitable oil components included those selected from the group consisting of fatty carboxylic acid esters, seed oils, petroleum oils, mono, di or tricarboxylic acids, fatty alcohols, fatty ethers, fatty amides, synthetic oils, and mixtures thereof.

The compositions and concentrates of the present invention may further comprise one or more monocarboyxlic acid esters. Suitable monocarboxylic acid esters include those having the following general formula: $R_2COOC_nH_{2n}+1$, wherein $R_2$ is an alkyl radical having from about 4 to about 22 carbon atoms, and n is a number from 1-4.

Suitable fatty acid esters include methyl and ethyl esters derived from the esterification of unsaturated carboxylic acids having from about 18 to 22 carbon atoms. Some preferred methyl esters include methyl oleate, methyl laurate, and methyl soyate. Some preferred ethyl esters include ethyl oleate, and ethyl canolate. Suitable fatty acids from which the fatty acid esters may be derived include coconut and other vegetable oils, tallow, etc. Di and tricarboxylic acids can also be used to form esters.

The compositions and concentrates of the present invention may further comprise alkoxylated carboxylic acid esters such as fatty acid esters including those listed above which are alkoxylated with ethylene oxide, propylene oxide, and combinations thereof.

The compositions and concentrates of the present invention may further comprise alcohols, including saturated or unsaturated alcohols and branch or linear alcohols. In some embodiments, the alcohols are $C_8$-$C_{20}$ alcohols.

The compositions and concentrates of the present invention may further comprise carboxylic acids including those having of a chain of alkyl groups containing from 4 to 22 carbon atoms, and characterized by a terminal carboxyl group. The carboxylic acids may be saturated such as, for example, butyric, lauric, palmitic, and stearic or unsaturated such as, oleic, linoleic, and linolenic.

The compositions and concentrates of the present invention may further comprise fatty ethers, which include those generally derived from fatty alcohols, such as those listed above, by the elimination of water. Fatty ethers are generally characterized by the formula ROR wherein R is an alkyl group containing from 4 to 22 carbon atoms.

The compositions and concentrates of the present invention may further comprise fatty amides including those of the general formula $R{=}CONH_2$ wherein R is an alkyl group having from 4 to 22 carbon atoms.

The compositions and concentrates of the present invention may further comprise seed oils are those derived from seeds and nuts and include castor, coconut, soybean, and the like. In some embodiments, the seed oil is or comprises soybean oil.

The compositions and concentrates of the present invention may further comprise petroleum oil which includes petroleum, petroleum-derived oils, and synthetic oils.

The compositions and concentrates of the present invention may further comprise a glyceride such as those derived from glycerol and $C_6$-$C_{22}$ fatty acids. In some embodiments, the glyceride is glycerol mono- and/or di-oleate.

The compositions and concentrates of the present invention may further comprise nonionic surfactants. Suitable nonionic surfactants include sugar surfactants, alkoxylated fatty alcohols, alkoxylated fatty acids, alkoxylated fatty acids, alkoxylated fatty ethers, alkoxylated fatty amides, ethoxylated seed oils, ethoxylated mineral oils, nonylphenol ethoxylates, alkoxylated alkyl phenols, ethoxylated glycerides, castor oil ethoxylates, and mixtures thereof.

Alkoxylated fatty alcohols include fatty alcohols such as those listed above which are alkoxylated with ethylene oxide, propylene oxide, and combinations thereof.

Alkoxylated fatty acids include fatty acids such as those listed above which are alkoxylated with ethylene oxide, propylene oxide, and combinations thereof.

Alkoxylated fatty ethers include fatty ethers such as that list above, which are alkoxylated with ethylene oxide, propylene oxide, and combinations thereof.

Alkoxylated fatty amides include fatty amides such as those listed above which are alkoxylated with ethylene oxide, propylene oxide, and combinations thereof.

Suitable alcohols ethoxylates included $C_8$-$C_{18}$ alcohols ethoxylated with from about 2 to about 30 moles of ethylene oxide.

Suitable ethoxylated seed oils include those containing from about 1 to about 200 moles of ethylene oxide.

Suitable nonylphenol ethoxylates include those ethoxylated with about 4 to about 70 moles of ethylene oxide. A particularly preferred nonylphenol ethoxylated is a combination of a NP-9 with an NP-6.

Other surfactants that may be included in the compositions and concentrates of the present invention include quaternary ammonium surfactants, ether amine surfactants, alkoxylated amine surfactants, secondary or tertiary alcohol surfactants, sorbitan fatty acid ester and amine, organosilicone surfactants, phosphate esters, and alkyl polyglycosides.

In some embodiments, the compositions and concentrates of the present invention comprise a fatty alkanolamide of the formula $$RCN\begin{matrix}O\\\|\end{matrix}\begin{matrix}R'\\ \diagup\\ \diagdown\\ R''\end{matrix}$$

wherein R is an alkyl group having from about 6 to about 25 carbon atoms; R and R" are the same or different and are independently selected from the group consisting of hydrogen, —CH$_2$CH$_2$OH, and $$-CH_2-\underset{\underset{CH_3}{|}}{CH}-OH$$

In some embodiments, the compositions and concentrates of the present invention comprise a PEG ester of the formula $$R^2\underset{\underset{O}{\|}}{C}-O(CH_2CH_2O)_mR^3$$

wherein $R^2$ is $C_2$-$C_{25}$ alkyl, $R^3$ is alkyl having from about 2 to about 25 carbon atoms or hydrogen and m is a number from 1 to about 100.

In some embodiments, the compositions and concentrates of the present invention comprise a silicone surfactant of the formula $$CH_3-\underset{\underset{CH_3}{|}}{\overset{\overset{CH_3}{|}}{Si}}-O-\left[\underset{\underset{CH_3}{|}}{\overset{\overset{CH_3}{|}}{Si}}-O\right]_x-\left[\underset{\underset{\underset{\underset{(C_2H_4O)_a(C_3H_6O)_bR^6}{|}}{O}}{(CH_2)_n}}{\overset{\overset{CH_3}{|}}{Si}}-O\right]_y-\underset{\underset{CH_3}{|}}{\overset{\overset{CH_3}{|}}{Si}}-CH_3$$

wherein x is a number from 0 to about 5, y is a number from 1 to about 5, a is a number from about 3 to about 25, b is a number from 0 to about 25, n is a number from about 2 to about 4 and $R^6$ is hydrogen, an alkyl group having 1 to about 4 carbon atoms or an alkyl ester group having 1 to about 4 carbon atoms.

In some embodiments, the compositions and concentrates of the present invention comprise an ethoxylated carboxylic acid of the formula $$R^7\underset{\underset{O}{\|}}{C}-O(CH_2CH_2O)_pH$$

wherein $R^7$ is an alkyl group having from about 6 to about 25 carbon atoms, p is a number from 1 to about 100.

In some embodiments, the compositions and concentrates of the present invention comprise an alkyl ethoxylates of the formula $$R^8O(CH_2CH_2O)_qH$$

wherein $R^8$ is an alkyl group having from 1 to about 50 carbon atoms and q is a number from 1 to about 100.

In some embodiments, the compositions and concentrates of the present invention comprise an alkylphenol ethoxylate of the formula $$R^9-\underset{\underset{R^{10}}{|}}{\bigcirc}-(OCH_2CH_2)_nOH$$

wherein $R^9$ is hydrogen or an alkyl having from about 1 to about 20 carbons atoms, $R^{10}$ is hydrogen or an alkyl having from about 1 to about 20 carbon atoms and n is a number from 1 to about 100.

In some embodiments, the compositions and concentrates of the present invention comprise a polypropylene glycol of the formula $$HO-(CH-CH_2-O)_{(1-t)}-\underset{\underset{CH_3}{|}}{\overset{\overset{CH_3}{|}}{CH_2}}-CHOH$$

wherein t is a number from 1 to about 100.

In some embodiments, the compositions and concentrates of the present invention comprise an amine ethoxylate of the formula $$R^{11}-N\begin{matrix}(CH_2CH_2O)_gH\\ \diagup\\ \diagdown\\ (CH_2CH_2O)_hH\end{matrix}$$

wherein g and h independently of one another are numbers from 1 to about 100 and R" is an alkyl having from 1 to about 25 carbon atoms.

In some embodiments, the compositions and concentrates of the present invention comprise a tristyrylphenol alkoxylate.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. A method for reducing or inhibiting spray drift and/or driftable fines of a composition, having at least one agrochemical or adjuvant, when sprayed onto a surface or increasing the amount of particles of the composition deposited onto the surface which comprises
adding a formulation comprising at least one resin to the composition, wherein the amount of the at least one resin in the composition is about 0.01% to about 0.10% by weight of the total composition and the at least one resin is selected from the group consisting of polyterpenes, alpha and beta terpenes, styrenated terpenes, alpha methyl styrene resins, and mixtures thereof, and spraying the composition.

2. The method according to claim 1, wherein the resin is, a polyterpene.

3. The method according to claim 1, wherein the composition comprises an agrochemical.

4. The method according to claim 1, wherein the composition further comprises at least one of the following emulsifiers, surfactants, fatty acids, pH modifiers, water conditioning agents, wetting agents, dispersants, solvents, preservatives, humectants, coupling agents, defoamers, and mixtures thereof.

5. A composition having reduced driftable fines which comprises at least one agrochemical and a formulation comprising at least one resin selected from the group consisting of polyterpenes, alpha and beta terpenes, styrenated terpenes, and mixtures thereof, and wherein the amount of the at least one resin in the composition is about 0.01% to about 0.10% by weight of the total composition.

6. The composition according to claim 5, wherein the resin is, a polyterpene.

7. The composition according to claim 5, wherein the resin is an alpha pinene, a beta pinene, or a mixture thereof.

8. The composition according to claim 5, wherein the agrochemical is a pesticide, a fungicide, a herbicide, an insecticide, or a fertilizer.

9. The composition according to claim 8, wherein the agrochemical is present in an amount of about 0.001% to about 99% by weight of the composition.

10. A method for treating an agricultural target which comprises spraying the composition according to claim 5 onto the surface of the agricultural target using a spraying apparatus.

11. A concentrate for reducing driftable fines of at least one agrochemical or adjuvant which comprises a concentrated amount of at least one resin and a concentrated amount of the at least one agrochemical or adjuvant, wherein the concentrated amount of the at least one resin is an amount that results in about 0.001% to about 0.10% when the concentrate is diluted to give an effective concentration of the at least one agrochemical or adjuvant suitable for spraying on an agricultural target, and wherein the at least one resin is selected from the group consisting of polyterpenes, alpha and beta terpenes, styrenated terpenes, and mixtures thereof.

12. The method of claim 1, wherein the amount of the at least one resin results in a reduction of about 1 percent to about 10 percent in the amount of driftable fines.

13. The composition of claim 5, wherein the amount of the at least one resin results in a reduction of about 1 percent to about 10 percent in the amount of driftable fines.

14. The composition according to claim 11, wherein the concentrated amount comprises about 1% to about 50% of the at least one resin.

15. The concentrate of claim 11, wherein the amount of the at least one resin results in a reduction of about 1 percent to about 10 percent in the amount of driftable fines.

* * * * *